United States Patent [19]
Brendel

[11] Patent Number: 5,320,714
[45] Date of Patent: Jun. 14, 1994

[54] POWDER INHALATOR

[75] Inventor: Gerhard Brendel, Munich, Fed. Rep. of Germany

[73] Assignee: Byk Gulden Lomberg Chemische Fabrik GmbH, Constance, Fed. Rep. of Germany

[21] Appl. No.: 920,423

[22] PCT Filed: Feb. 16, 1991

[86] PCT No.: PCT/EP91/00303
§ 371 Date: Aug. 14, 1992
§ 102(e) Date: Aug. 14, 1992

[87] PCT Pub. No.: WO91/12040
PCT Pub. Date: Aug. 22, 1991

[30] Foreign Application Priority Data

Feb. 16, 1990 [DE] Fed. Rep. of Germany ....... 4004904

[51] Int. Cl.$^5$ ............................................. A61M 15/00
[52] U.S. Cl. .............................. 128/203.15; 128/203.23
[58] Field of Search .............. 128/203.15, 203.19, 128/203.21, 203.23, 203.12, 200.24, 200.23; 222/344, 345, 346, 367; 604/58

[56] References Cited

U.S. PATENT DOCUMENTS

| 2,432,946 | 12/1947 | Theunissen | 128/206.21 |
| 2,540,059 | 1/1951 | Stirn et al. | 141/1 |
| 2,622,594 | 12/1952 | Brooks | 128/203.15 |
| 3,464,469 | 9/1969 | Belz | 222/390 X |
| 3,554,412 | 1/1971 | Hayashi et al. | 222/346 |
| 3,656,518 | 4/1972 | Aronson | 141/1 |
| 4,047,525 | 9/1977 | Kulessa | 128/203.15 |
| 4,428,709 | 1/1984 | Peters | 128/203.15 X |
| 4,721,233 | 1/1988 | Asada | 222/245 |
| 5,033,463 | 7/1991 | Cocozza | 128/203.21 |
| 5,113,855 | 5/1992 | Newhouse | 128/203.12 |
| 5,176,132 | 1/1993 | Drought et al. | 128/203.15 |

FOREIGN PATENT DOCUMENTS

| 2926659 | 1/1981 | Fed. Rep. of Germany | 128/203.15 |
| 4004904A1 | 9/1990 | Fed. Rep. of Germany . | |
| 848035 | 7/1981 | U.S.S.R. | 128/203.15 |
| 2041763A | 9/1980 | United Kingdom . | |

Primary Examiner—Edgar S. Burr
Assistant Examiner—Eric P. Raciti
Attorney, Agent, or Firm—Feiereisen & Kueffner

[57] ABSTRACT

A powder inhaler includes a housing with a reservoir for a powdery drug and a gas passage duct extending through the housing. A metering device is provided for supplying metered quantities of the powdery drug from the reservoir to the gas passage duct. A secondary flow separating chamber is arranged in communication with the gas passage duct.

4 Claims, 1 Drawing Sheet

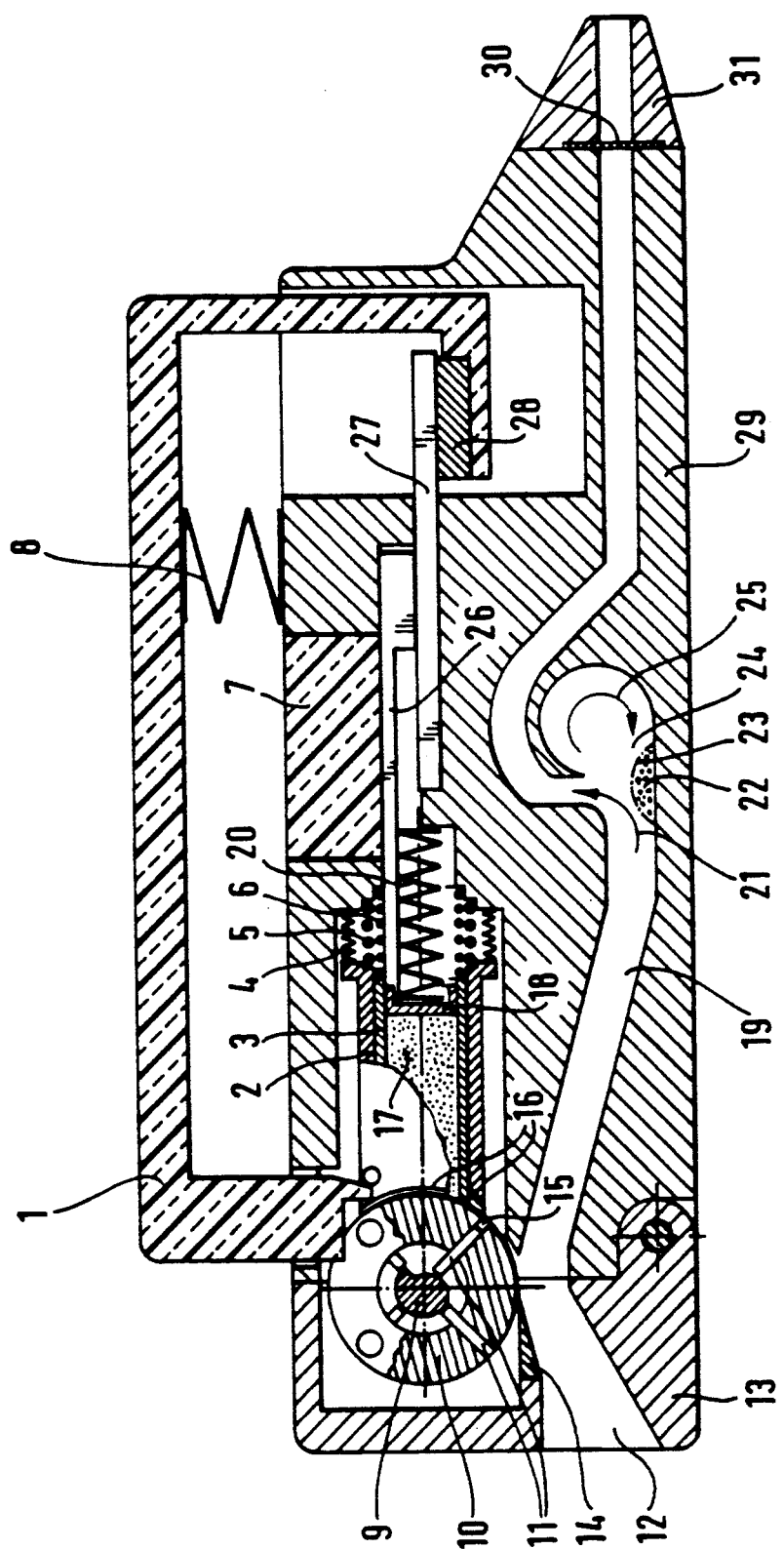

POWDER INHALATOR

FIELD OF THE INVENTION

The invention relates to a powder inhaler including a reservoir for powdery drugs, a metering device and a gas passage duct.

PRIOR ART

Numerous powder inhalers are known. A problem in the known powder inhalers is the insufficient protection against air humidity and the division, which is made difficult as a result of the latter, of a powdery drug conglomerate under the effect of flow of a gas or gas mixture into small particles, whose size must be within appropriate limits so that they can pass into the sites of action intended for them in the human respiratory tract. Operation of the known powder inhalers is complicated, as a result of which use by handicapped people and use in situations of stress are not guaranteed. Additionally, an indication of the remaining quantity of the drug which can still be applied would be desirable. In known powder inhalers, there is the risk of dose fluctuations. Furthermore, in terms of their constructional size, known powder inhalers exceed pocket size and thus comply only to a limited extent with appropriate practical use.

DESCRIPTION OF THE INVENTION

One object of the invention is seen in achieving an application of powdery drugs by inhalation with the greatest possible certainty of application as the result of simple, invariable sequence of operation and precise metering by pushing the button only once. Moreover, it is to be possible for the application, that is to say the inhalation, to take place independently of the state of the button triggering the metering, that is to say it is to be possible for the button to remain pressed during the application or to be released previously.

A further aim of the invention consists in designing the exchange of the drug reservoir to be simple and inevitable and in not permitting operation errors. Additionally, the drug reservoir is to be implementable with the least amount of material and with simple contours in order to achieve cost-effect refilling with drugs, a low material weight relative to the volume to be received and a small amount of packaging. In addition to precise metering of the drug, the drug powder is to be separated to the largest possible extent during the application. Additionally, the powder applicator is to be as easy as possible to clean, for example by a jet of water.

These objects are achieved by powder inhalers including a reservoir for powdery drugs, a metering device and a gas passage duct.

It has been shown that an improved separation of powder agglomerates of active substances can be achieved by a secondary flow separating chamber. This leads to a greater proportion of the drug being deposited not in the mouth and throat area, but at the desired destination in the lung.

The subject of the invention is therefore constituted by powder inhalers, in which the gas passage duct communicates with a secondary flow separating chamber.

A further subject of the invention is constituted by powder inhalers, whose metering device consists of a metering drum, which can be rotated about a camshaft, having rams which are displaceable perpendicular to the axis of rotation through the camshaft in openings in the wall of the metering drum which is rotated further through the angle between two rams in each case when the push-button is actuated.

A further subject of the invention is constituted by powder inhalers, whose reservoir is mounted in a guide bush and is pressed by a compression spring against the metering drum in an interlocking manner.

A further subject of the invention is constituted by powder inhalers, in which a movable substrate plunger is provided in the reservoir, which substrate plunger is loaded by a substrate spring as soon as the powder inhaler is activated by a push-button.

BRIEF DESCRIPTION OF THE DRAWING

The single FIGURE of the drawing is a schematic sectional view of the powder inhaler according to the present invention.

DESCRIPTION OF THE PREFERRED EMBODIMENT

A push-button 1 is integrated in the housing 29 of the powder inhaler. Said push-button is pushed upwards by the compression spring 8 into its position of rest. The metering drum 10 is mounted rotatably in the hinged rear part 13 of the housing. Said metering drum has the shape of a thick-walled cylinder with openings through the cylinder wall. Movable rams 11, corresponding to the shape of the cross section of the opening, are mounted in these openings in such a way that they constantly bear against a camshaft 9 and thus expose a volume 15 on the surface of the metering drum 10, which volume depends on the respective position of the ram 11 relative to the camshaft 9. The guide bush 2 for the reservoir 3 is pressed with its seal 16 by the compression spring 5 against the metering drum 10 in an interlocking manner. The guide bush 2 for the reservoir 3 is sealed off in relation to the housing by the folding seal 4. The guide bush 2 for the reservoir 3 can be circular, oval or polygonal in cross-section and receives the reservoir 3 which can correspondingly likewise be circular, oval or polygonal in cross-section. The reservoir 3 is constantly pressed by the compression spring 6 against the metering drum 10 in an interlocking manner. Upon actuation of the push-button 1 and interruption associated therewith, of the magnetic flow from the magnet 28 via the iron magnetic conductor coupling 27 on to the coupling bar 26, the substrate spring 20 presses the substrate plunger 18 with slight spring force against the powdery drug 17. An indication of the quantity remaining is possible through a transparent cutout 7 by appropriate marking of the coupling bar 26. Moreover, complete filling of the volume 15 on the surface of the metering drum 10 is thereby achieved. By converting the lifting movement to a rotary movement, the actuation of the push-button 1 leads to a rotation of the metering drum 10 through the angle between two adjacent rams 11. If there are four rams 11, the actuation of the push-button 1 leads to a quarter-rotation of the metering drum 10. At the same time, the guide bush 2 for the reservoir 3 is moved away from the metering drum 10 by the push-button 1 in order to release the seal 16 between the metering drum 10 and the guide bush 2 for the reservoir 3. At the same time, the magnet 28 is released from the magnetic conductor coupling 27 and thus cancels the magnetic fixing of the coupling bar 26. The spring force of the substrate spring 20 acts on the substrate plunger 18 only during this period of the push-button 1 being pressed. The volume 15 produced on the surface of the metering drum 10—caused by the position of the camshaft 9 relative to the ram 11—is filled with the powdery drug 17 which is ejected again by the ram 11 near to the end of the rotary movement of the metering drum 10 and can be scraped off by a scraper 14. On return of the push-button 1 into its position of rest, the guide bush 2 for the reservoir 3 is again pressed with its seal 16 against the metering drum 10 by the compression spring 5. The reservoir 3 constantly remains pressed against the metering drum 10 by the compression spring 6 during the entire removal operation and thus remains closed even during removal. The entry of air 12 in the rear part 13 of the housing takes place by inspiration at the mouthpiece 31 and, due to the flow pressure, carries along the drug scraped off at the scraper 14. Due to the shaping of the flow duct 19, a main flow 21 of air and a secondary flow 25 of air are produced. Heavy drug conglomerates 22, which have not yet been atomized to an appropriate size, cannot follow the main flow 21 of air due to their weight and are swirled in the secondary flow separating chamber 24. Agglomerates are carried from the path and remain in the atomizing region 23 until they have been atomized to the extent that they can be carried along by the flow pressure. The flow pressure is determined by the width of the flow duct 19 and can thus be adjusted to different sizes. Due to the great width and thus low flow pressure at the entry of the secondary flow separating chamber 24, the drug conglomerates 22 are reliably flung from the path and can only be carried along by the increased flow pressure in the case of narrow width of the flow duct above the secondary flow separating chamber 24, if they are light enough to pass into its suction region. They then pass through the filter 30 and arrive in the regions corresponding to their size in the human respiratory tract.

I claim:

1. A powder inhaler comprising a housing having an axis, the housing defining a reservoir for a powdery drug and a gas passage duct extending essentially in axial direction through the housing, the housing comprising a first opening of the gas passage duct for taking air into the gas passage duct and a second opening of the gas passage duct for inhaling air from the gas passage duct and for producing a primary air flow in the gas passage duct in a flow direction, further comprising a metering device for supplying metered quantities of the powdery drug from the reservoir into the gas passage duct, the gas passage duct having at a location between the first and second openings a bend portion in which bend portion the gas passage duct is curved from the axial direction to an upward direction transversely of the axial direction, the gas passage duct further having an upwardly directed gas passage duct portion following the bend portion in flow direction, and an essentially circular secondary flow separating chamber arranged in communication with an essentially tangentially to the bend portion of the gas passage duct, such that a lighter fraction of the powdery drug is conducted by the primary air flow through the bend portion and the upwardly directed portion of the gas passage duct and a heavier fraction of the powdery drug is conducted into and swirled within the secondary flow separating chamber.

2. The powder inhaler according to claim 1, the metering device comprising a cam shaft having an axis of rotation, a metering drum rotatably mounted on the cam shaft, the metering drum having a wall defining openings, rams mounted in the openings so as to be displaceable by means of the cam shaft in a direction extending perpendicularly to the axis of rotation of the cam shaft, an angle being defined between adjacent openings, and a push-button in operative connection with the metering drum for rotating the metering drum by the angle between two openings.

3. The powder inhaler according to claim 2, wherein the reservoir is mounted in a guide bush, further comprising a compression spring for pressing the reservoir against the metering drum in an interlocking manner.

4. The powder inhaler according to claim 3, further comprising a movable substrate plunger mounted in the reservoir, a substrate spring connected to the substrate plunger, and means for loading the substrate plunger by the substrate spring when the push-button is activated.

* * * * *